(12) United States Patent
Siebert et al.

(10) Patent No.: US 6,613,212 B1
(45) Date of Patent: Sep. 2, 2003

(54) MULTIPLE CAPILLARY ELECTROPHORESIS SYSTEMS

(75) Inventors: Rainer Siebert, Les Clayes-sous-Bois (FR); Samuele Bottani, Paris (FR); Hans Rebscher, Mannheim (DE); Luc Valentin, Bures (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/402,219

(22) PCT Filed: Jan. 29, 1999

(86) PCT No.: PCT/FR99/00184

§ 371 (c)(1),
(2), (4) Date: Feb. 7, 2000

(87) PCT Pub. No.: WO99/39192

PCT Pub. Date: Aug. 5, 1999

(30) Foreign Application Priority Data

Jan. 30, 1998 (FR) .............................................. 98 01091

(51) Int. Cl.$^7$ ......................... C02F 1/40; G01N 33/48; G01N 21/29; G01N 21/64; G01N 21/66
(52) U.S. Cl. .................. 204/603; 204/600; 204/601; 204/452; 436/43; 436/63; 356/344; 250/458.1; 422/50; 422/68.1; 422/82.05; 422/82.08
(58) Field of Search ................. 204/600, 601, 204/603, 604, 452; 436/63; 356/344; 250/458.1; 422/50, 68.1, 82.05, 82.08

(56) References Cited

U.S. PATENT DOCUMENTS

| 5,324,401 A | | 6/1994 | Yeung et al. |
| 5,567,294 A | | 10/1996 | Dovichi et al. |
| 5,616,228 A | * | 4/1997 | Nasu et al. ................. 204/603 |
| 5,667,656 A | | 9/1997 | Kambara |
| 5,833,827 A | * | 11/1998 | Anazawa et al. ........... 204/603 |
| 5,938,908 A | | 8/1999 | Anazawa et al. ........... 204/603 |
| 6,063,251 A | * | 5/2000 | Kane et al. .................. 204/601 |
| 6,103,083 A | * | 8/2000 | Merenkova et al. ........ 204/603 |
| 6,191,425 B1 | | 2/2001 | Imai ........................ 250/458.1 |
| 6,224,733 B1 | * | 5/2001 | Takahashi et al. .......... 204/603 |

FOREIGN PATENT DOCUMENTS

| DE | 19616824 | 5/1997 |
| EP | 0723149 | 7/1996 |
| GB | 2312505 | 10/1997 |
| GB | 2314622 | 1/1998 |
| WO | WO94/29712 | 12/1994 |
| WO | WO9634278 | 10/1996 |
| WO | WO9636872 | 11/1996 |

OTHER PUBLICATIONS

Dovichi N J: "Laser–based Microchemical analysis" review of scientific instruments, vol. 61, No. 12, Dec. 1, 1990 pp. 3653–3667.

J.A. Taylor et al.: "Axial–beam absorbance detection for capillary electrophoresis" Journal of Chromatography, vol. 550, No. 1/2, 1991, pp. 831–837.

* cited by examiner

*Primary Examiner*—Jill Warden
*Assistant Examiner*—Brian Sines
(74) *Attorney, Agent, or Firm*—Blakely, Sokoloff, Taylor & Zafman (57) ABSTRACT

The invention concerns a multiple capillary electrophoresis system including many juxtaposed capillaries, at least one source for transmitting a beam designed to excite the molecules present in its path and inside the capillaries, and detection of the fluorescence of the molecules excited by said beam. The invention is arranged so as to detect the light emerging at the output of said capillaries and propagated along a direction wherein the capillaries extend and the detection resolution is sufficient for distinguishing the light emerging at the output of the capillaries from that coming from the walls thereof and/or their surrounding medium.

13 Claims, 9 Drawing Sheets

FIG_1

FIG_6a    FIG_6b

FIG_7a    FIG_7b

FIG_11

FIG_12a

FIG. 12b

MULTIPLE CAPILLARY ELECTROPHORESIS SYSTEMS

The present invention relates to multicapillary electrophoresis systems.

It is known that conventional gel electrophoresis techniques, in which various samples are injected along a plurality of tracks defined in a gel placed between two plates, are not satisfactory, given that, on the one hand, they require a number of manual operations and, on the other hand, they do not allow very high migration velocities and therefore very high treatment throughputs.

However, the major sequencing and genotyping programs require a very high rate of separation and identification of DNA molecules.

Moreover, electrophoresis techniques are known which use, for the migration, a capillary filled with gel or with another separating matrix having the advantage of being particularly handleable, easy to load and which allow substantially automatic operation, with higher separation rates than in electrophoresis using gel slabs by virtue of a high electric field that can be applied.

However, the use of a single capillary does not make it possible to achieve the same rates as those allowed by electrophoresis techniques using slabs which possess many parallel tracks, even if nevertheless the electric fields that can be applied to a capillary, and therefore the migration velocities obtained, are high.

This is why systems called multicapillary systems comprising a linear array of several juxtaposed capillaries have also been proposed.

In particular, multicapillary electrophoresis systems are known in which the laser beam for exciting the molecules is sent into the capillaries through their walls, along an axis in the plane of the linear array, perpendicular to the direction along which the capillaries extend, the fluorescence of the molecules being observed by receiving means having an optical axis perpendicular to the plane of the linear array of capillaries.

In this regard, reference may be made, for example, to the publication: "A Capillary Array Gel Electrophoresis System Using Multiple Laser Focusing For DNA Sequencing"—T. Anazawa, S. Takahashi and H. Kambara, Anal. Chem., Vol. 68, No. 15, Aug. 1, 1996, pp. 2699–2704.

However, such a technique is not very satisfactory on account of the detection noise resulting from the interaction of the excitation light and the fluorescence from the walls of the capillary. Furthermore, the laser beam loses intensity as it passes through the capillaries, so that the molecules which are located in the capillaries furthest from the laser source are less excited than those moving in the first capillaries.

Because of these major drawbacks, the systems of the type of those described in the publication: "Analysis of Nucleic Acids by Capillary Electrophoresis" by C. Heller, pp. 236 to 254, Editions Vieweg, 1997, or else in the patents and patent applications U.S. Pat. No. 5,567,294 or EP-723, 149, are generally preferred to multicapillary electrophoresis systems in which the laser beam for exciting the molecules is sent into the latter through the walls of the capillaries.

In the systems described in that publication or those patents, the capillaries are held one with respect to the other in a glass cuvette along which said capillaries extend. The molecules which travel along the capillaries are excited after having exited said capillaries by a beam of laser radiation which is sent, just at the exit of the linear array, in the plane of said linear array and perpendicular to the direction along which the capillaries extend.

The fluorescence of the molecules excited by this radiation is detected, for example, by means of a CCD camera which is oriented with an axis perpendicular to the plane of the linear array of capillaries or else with an axis parallel to the capillaries.

However, such a system requires means to be provided, such as laminar flow means or guiding elements, which prevent the molecules from diverging too significantly at the exit of the various capillaries. To do this, the cuvette requires a high-precision mechanical construction in glass. In particular, the device will have to provide a very uniform flow and avoid any gas bubbles or dust disturbing the flow.

Furthermore, this technique requires the use of different materials—at least as regards the viscosity—for the capillaries and the cuvette, which have different functions, one serving for separating the molecules and the other for channeling the flows. It therefore becomes necessary to use large volumes of solutions to produce the flow.

As will have been understood, such a technique has the drawback of being particularly expensive.

One aim of the invention is therefore to propose a multicapillary electrophoresis system which, for chemical and pharmaceutical applications, is robust, inexpensive, reliable and easy to use and whose performance allows high-throughput sequencing and genotyping.

For this purpose, the invention proposes a multicapillary electrophoresis system comprising a plurality of juxtaposed capillaries, at least one source for the emission of a beam intended to excite molecules lying in its path and inside the capillaries and means for detecting the fluorescence of the molecules excited by said beam.

In order to alleviate the drawbacks which, in the known systems in the prior art, caused those skilled in the art to move away from this type of system, the invention proposes to arrange the detection means so as to detect the light which emerges at the exit of said capillaries and which propagates along the direction in which said capillaries extend, as well as to use detection means having a high enough resolution to distinguish the light which emerges at the exit of the capillaries from that coming from the walls of the latter and/or from the medium which surrounds them.

Such a structure makes it possible to detect molecules inside the capillaries while considerably reducing the detection noise.

This system is advantageously completed by the following various advantageous characteristics taken by themselves or in any of their technically possible combinations:

- it includes a matrix of capillaries;
- it includes means, such as microlenses, for producing multiple focusing on a linear array of capillaries;
- one linear array of capillaries produces multiple focusing at the entry of the following linear array;
- the excitation beam is of elongate cross section and strikes several superposed capillaries simultaneously;
- the space between the capillaries is filled, at least along the path of the excitation beam, by a material whose refractive index is chosen so that the excitation beam does not diverge after having traveled along a capillary;
- said material is transparent and non-fluorescent;
- it includes means for applying pressure in the detection cuvette, which pressure allows the capillaries to be filled with the separating matrix;
- it includes dispersion means for spatially separating the various fluorescence wavelengths;
- the detection means provide a complete image of the light exiting the capillaries;

the detection means comprise detection means of the charge-coupled device (CCD) type, as well as focusing means;

the detection means comprise detection means of the charge-coupled device (CCD) type, as well as a fiber bundle interposed between the exits of the capillaries and the detection means of the charge-coupled device type.

Further features and advantages of the invention will also emerge from the description. This description is purely illustrative and non-limiting. It must be read with regard to the appended drawings in which.

Figure 1:
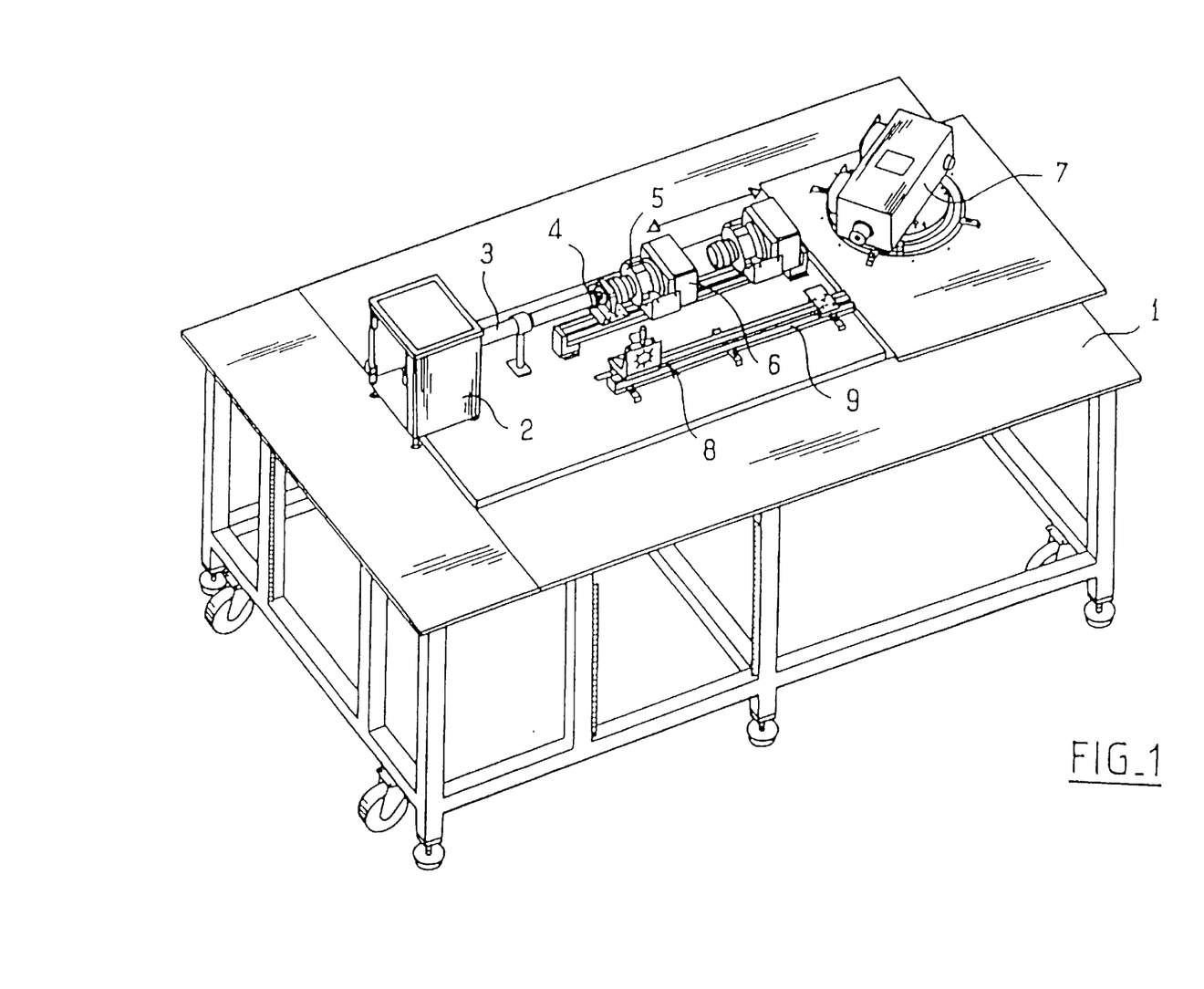
FIG. 1 is a schematic perspective representation of a system in accordance with one possible embodiment of the invention.

The multicapillary electrophoresis system shown in FIG. 1 comprises, on an optical table 1:

a channel 3 along which the capillaries extend;

a high-voltage box 2 with heating, on which box the capillary entries are mounted and into which a temperature control system is integrated;

a detection cell 4 placed at the exit of the channel 3;

a CCD camera 6 and a convergence optic 5 which are interposed between said camera 6 and the detection cell;

a laser source 7;

optical means 8 which are mounted on a rail 9 and which allow the beam from the source 7 to be directed onto the detection cell 4.

Figures 2, 3A, 3B:
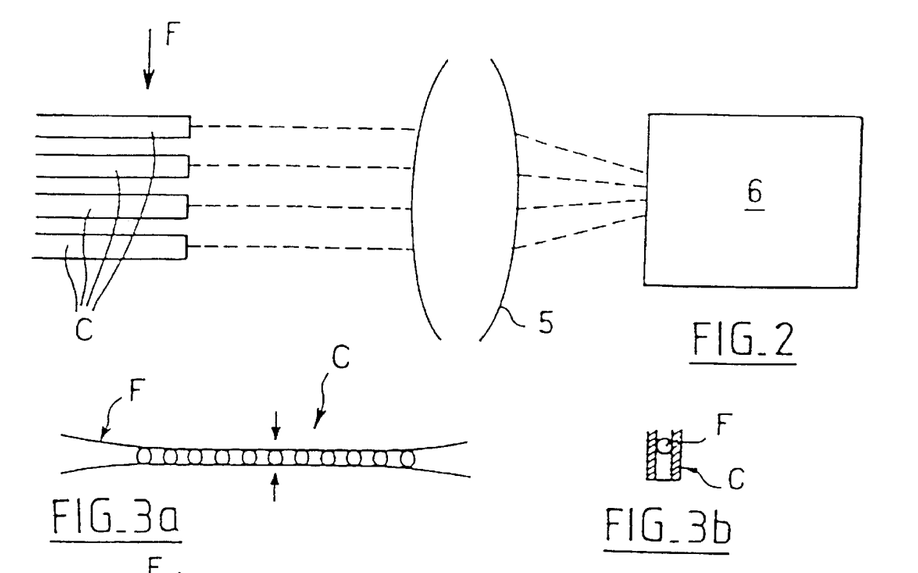
FIG. 2 is a schematic representation illustrating the arrangement of the detection means with respect to the capillaries for the system of FIG. 1.
FIGS. 3a and 3b illustrate the use of an excitation beam of circular cross section.

As is more particularly illustrated in FIG. 2, the CCD camera 6 observes the fluorescence of the molecules excited inside the capillaries by the laser beam F along an optical axis which is parallel to the axis of the capillaries C. The CCD camera 6 collects the fluorescence light coming directly from the excited molecules, which light forms a cone around the axis of said capillary over the solid angle between the position of the excited molecules in the capillary and the opening of said capillary.

As long as the resolution of the camera is high enough, this allows the light emerging from the inside of the capillaries C to be distinguished from that coming from the walls of the latter and/or from the medium which surrounds them. As a result, the signal-to-noise ratio is considerably improved.

For example, in the case of capillaries C having an internal diameter of 100 μm and an external diameter of 300 μm, it is possible to use, as detector, a CCD camera 6 providing, in combination with the optical means 5, a resolution of the order of 20 μm.

In addition, to minimize the background noise coming from the scattering of the laser beam F or the fluorescence of the walls of the capillaries C or the surrounding medium, a black mask forming a diaphragm is advantageously mounted at the exit of the capillaries C.

It will be noted, given that the fluorescence of the molecules is observed at the exit of the capillaries C along an axis parallel to the direction of the capillaries C, it becomes possible to use matrices of capillaries C, thereby allowing the electrophoresis efficiency to be considerably increased. The term matrix should be understood in a general manner and it denotes any assembly of capillaries C in which the latter are distributed in a superposed fashion with respect to one another in two directions. This term consequently encompasses matrices consisting of several superposed linear arrays just as well as other arrangements of capillaries and especially, for example, assemblies in which the capillaries are distributed in a staggered fashion.

The number of capillaries per matrix may vary greatly. Tests have been carried out on matrices of 16, 50 and 100 capillaries. A greater number of capillaries per matrix could also be envisioned.

The excitation beam F emitted by the laser source 7 is sent onto the detection cell 4, in order to strike the capillaries C perpendicular to the direction along which they extend.

The excitation beam F may then be either circular in cross section (FIGS. 3a and 3b), in which case it is sent in the plane of a linear array of capillaries C in order to pass in succession through the latter.

Figure 4A:
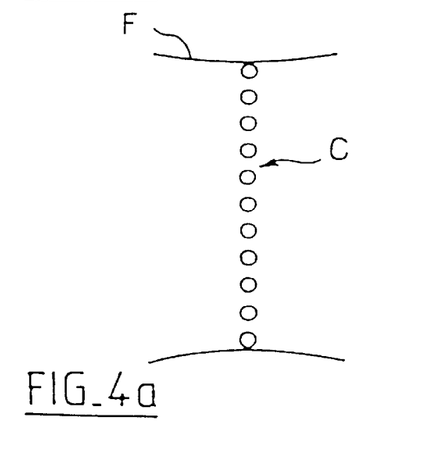
FIGS. 4a and 4b illustrate the use of a beam of elliptical cross section.
Figure 4B:
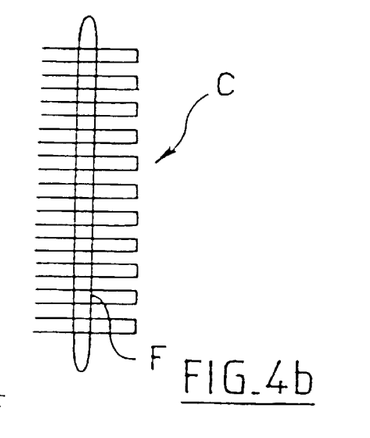

Also advantageously, it may be elongate (for example elliptical) and strike a linear array in an optical direction perpendicular to the plane of said linear array, thereby allowing the same beam F to strike the various superposed capillaries C simultaneously (FIGS. 4a and 4b). Furthermore, this allows a greater tolerance on the relative position of the capillaries.

Figure 5:
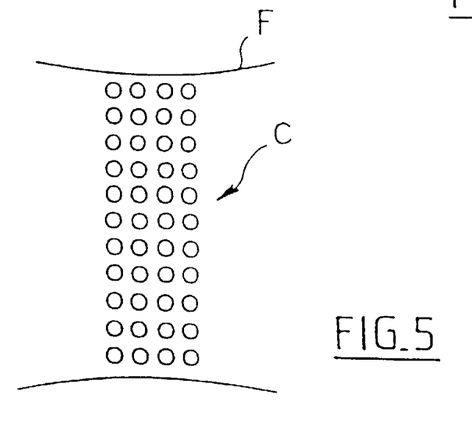
FIG. 5 illustrates the use of a matrix of capillaries.

In addition, as illustrated in FIG. 5, it will be advantageous to use an elliptical beam F when the capillaries C are distributed not in a linear array but in a matrix.

The capillaries C may be held together by bonding and/or by performs.

Figure 6A:
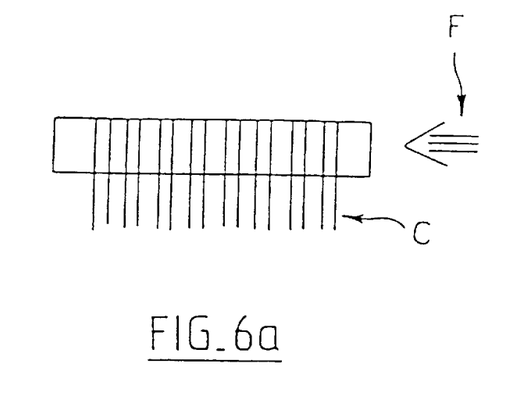
FIGS. 6a and 6b illustrate two possible variants for mounting the capillaries.
Figure 6B:
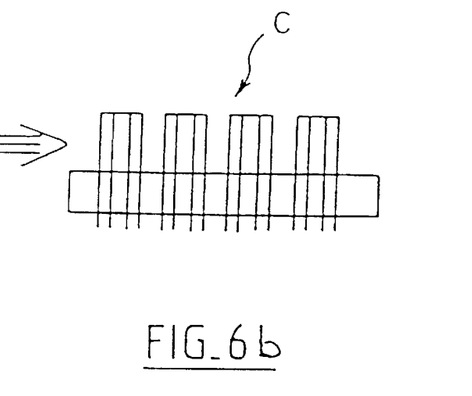

Moreover, as illustrated in FIG. 6a, it is possible to provide, along the path of the excitation beam, in the interstices between the capillaries C, a material whose refractive index is chosen so that the excitation beam does not diverge after having been crossed by a capillary, especially a material whose index is less than that of the capillaries.

This material is also chosen to be as transparent as possible and non-fluorescent.

Figure 7A:
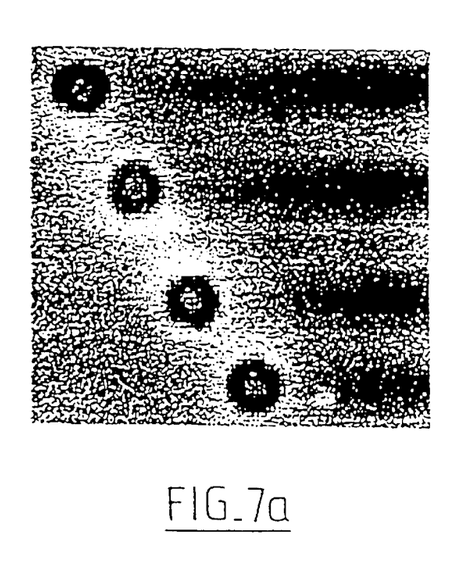
FIGS. 7a and 7b are two photographs illustrating the distribution of the excitation beam after it has traveled along the capillaries, depending on the index of the medium which surrounds the capillaries and through which said excitation beam travels.
Figure 7B:
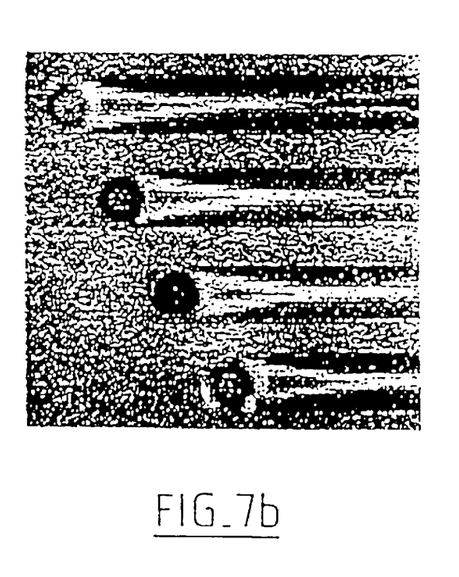

The focusing effect obtained with such a material is illustrated by the photographs given in FIGS. 7a and 7b. It may be seen in these photographs that a beam F illuminating several capillaries C in parallel creates shadow regions after passing through the capillaries C when the indices of the capillaries C and of the surrounding medium are similar, but that the light transmitted is focused when the external index is less than that of the capillaries C. Thus, the light at the exit of each of the capillaries is focused onto the capillary of the next row, which is directly opposite.

This multiple focusing makes it possible, for example, to use the same elliptical beam F to illuminate various rows of capillaries C.

This focusing effect also allows the laser beam to be used in an advantageous manner. Almost all of its intensity is focused in the various capillaries.

Such focusing can be achieved using an array of capillaries or else more perfectly by microlenses. This focusing decreases the power of the laser necessary by at least a factor of 3, creating at the same time less noise.

The material which provides the focusing function may optionally consist of the material which serves for fixing the capillaries. However, it is preferred to use the solutions in which, in order to prevent divergence of the excitation beam which crosses the capillaries, a material different from that used for fixing the capillaries.

Moreover, as illustrated in FIG. 7b, it will be noted that in this case the material which prevents the divergence of the excitation beam may consist of the buffer solution bathing the capillaries.

Technical details are given below relating to the set-up illustrated in FIG. 1, which was used by the inventors.

The electrode in the box 2 is supplied by a voltage generator sold by the company SPELLMAN.

The entries and exits of the capillaries C are electrically connected via a buffer or a polymer solution to the cathode and to the anode of this generator.

The voltage applied to the cathode may range up to 30 kV for a length of capillaries C of between 15 and 60 cm, the anode being at earth potential.

The detection cell 4 from which the capillaries C emerge is a rectangular parallelepiped with opaque walls, provided with two lateral quartz windows for the entry and exit of the laser beam F, while another window, also made of quartz, lies on the axis of the capillaries C in order to allow the fluorescence light to be collected by the optic 5 and the camera 6.

This latter window may be replaced with a filter in order for the fluorescence light to be discriminated from the laser light. As a variant, this filter may be placed at the exit of said window.

A fourth window, in the upper wall of the cell allows the alignment of the laser beam F with respect to the capillaries C to be observed.

The adhesive used for fixing the capillaries C in the detection cell is a transparent UV-curable adhesive.

The optic 5 is an objective which has a focal length of 1.2 [lacuna]. It is advantageously completed by two auxiliary lenses with a total of six diopters, in order to obtain a magnification close to 1.

Alternatively, the optic 5 may consist of two objectives, the first of which is inverted. A multicolor dispersion system is advantageously mounted between the two objectives.

Also as a variant, the optic 5 may advantageously incorporate a fiber-optic bundle interposed between the exits of the capillaries and the CCD camera.

The CCD camera 6 is of the type of those sold by PRINCETON under the name "frame transfer". It allows successive acquisitions to be made without dead time and without a mechanical shutter.

The active area of the camera is 6 to 8 mm$^2$ with a pixel size of 22 $\mu$m/22 $\mu$m.

The camera is cooled down to approximately $-40°$ C. by the Peltier effect.

The laser is an argon laser (from ILT) having a maximum power of approximately 100 mW at a wavelength of 488 nm.

A holographic prism allows any wavelength other than this 488 nm wavelength to be eliminated.

The separating matrix (a gel or other material) is injected into the capillaries by means of a pump which allows pressure to be applied in the detection cuvette.

Presented below are the results which were obtained with such a system, for a power of 40 mW of the laser beam F and a distance of 750 $\mu$m between the exit faces of the capillaries C and the point of impact of the detection excitation beam F, by injecting, electrokinetically or with a hydrodynamic flow, dilutions of oligonucleotides of a known concentration.

Figure 8:
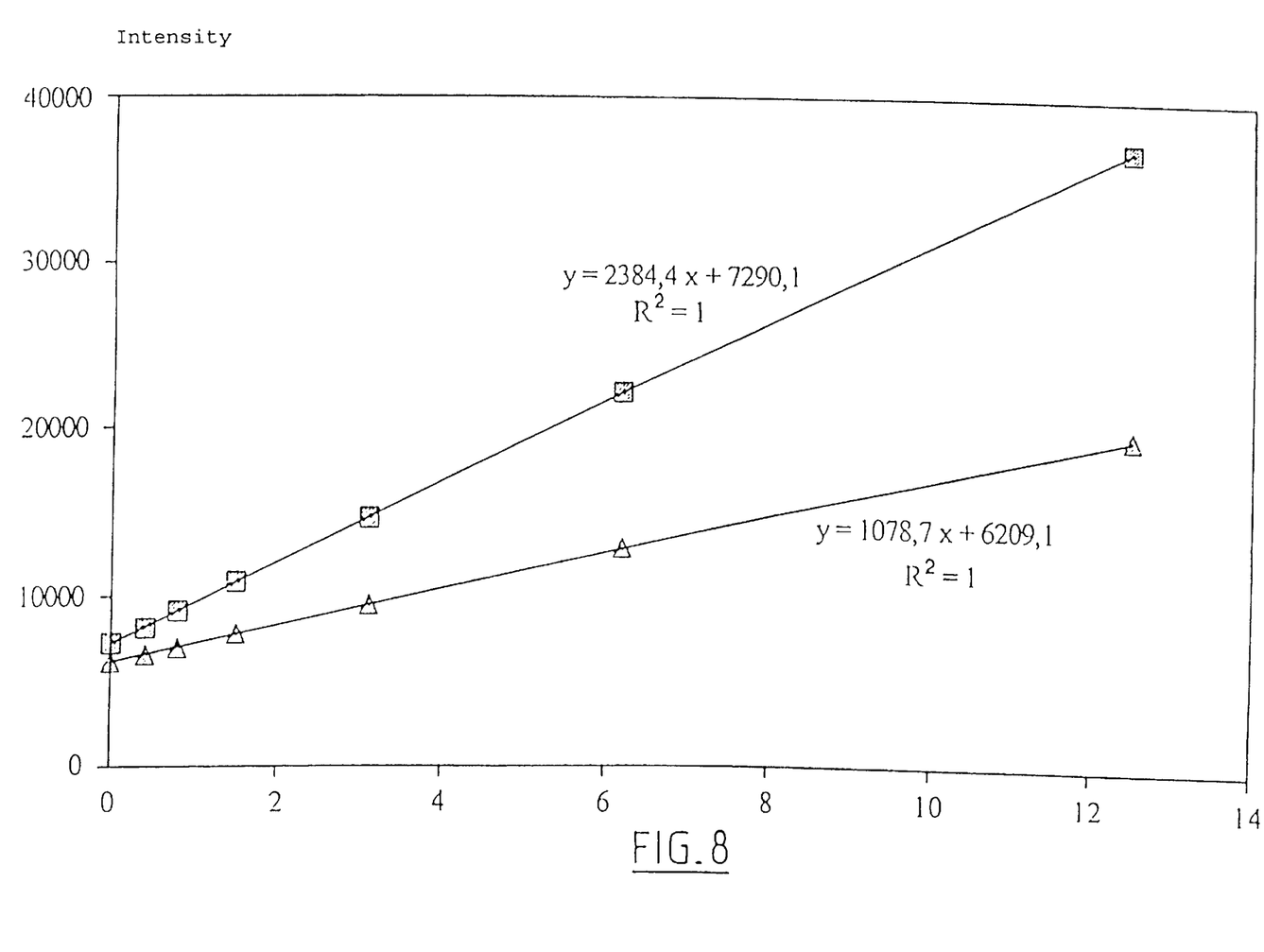
FIG. 8 is a graph on which the response of the system has been plotted as a function of the concentration of fluorescein.

FIG. 8 gives the number of charges collected on 25 pixels (summation by the software) as a function of the concentration of fluorescein sulfate injected. Good linearity is observed in the region shown, which has been checked between 0.05 and 100 nmol/l. The two straight lines correspond to the charges collected for a central capillary and one at the edge of the row, respectively. The difference is explained by the Gaussian distribution of the laser beam (conventionally elliptical).

Figure 9:
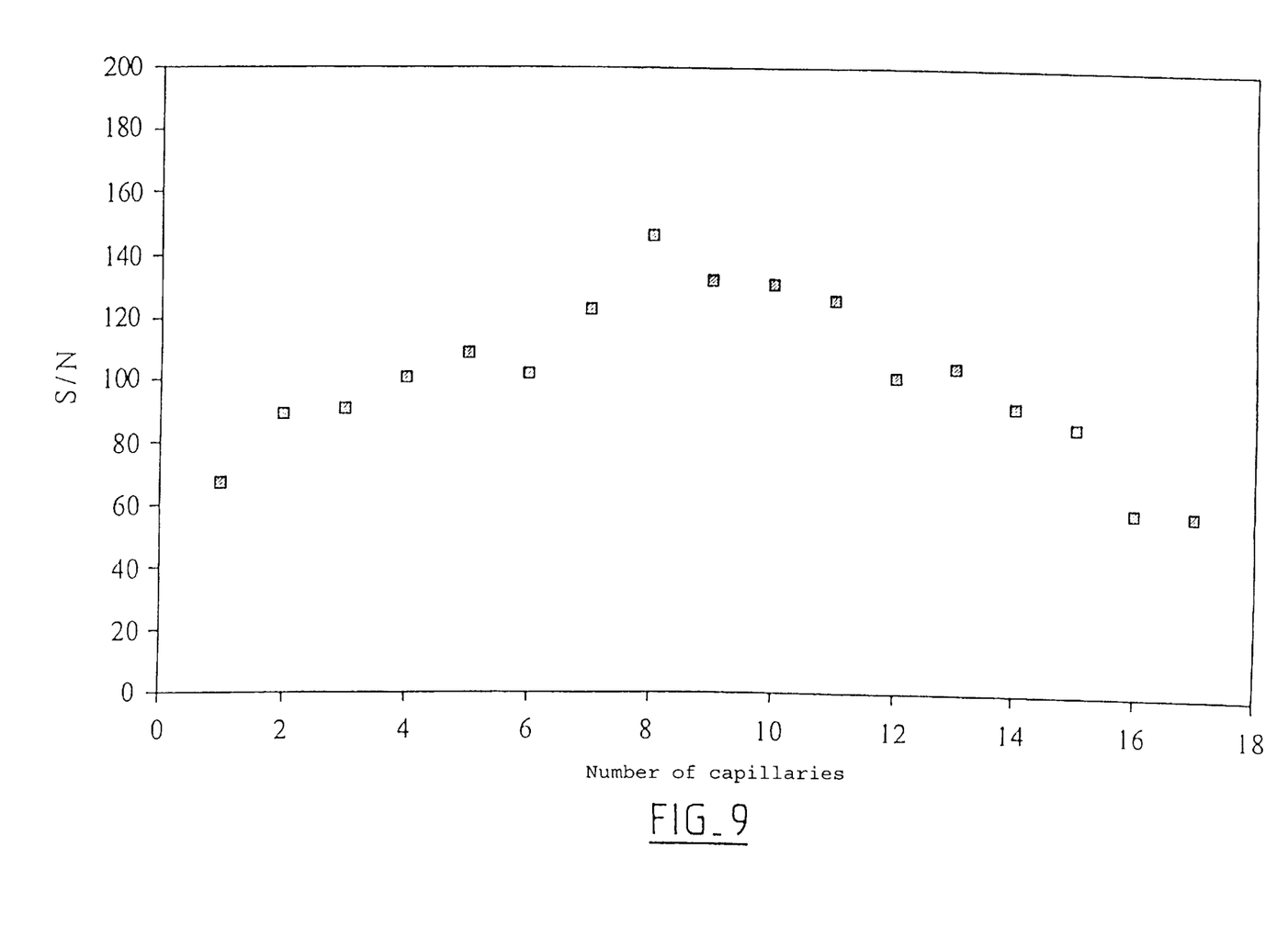
FIG. 9 is a graph on which the signal/noise ratio per capillary has been plotted.

With regard to the minimum detectable sensitivity, FIG. 9 gives the signal/noise (S/N) ratio as a function of the capillary number, obtained for a concentration of 1 nmol/l of fluorescein. A signal/noise ratio of greater than 50 is observed. Even seen from the edge, this ratio is broadly satisfactory for sequencing or genotyping experiments.

In order to improve the sensitivity further, larger pixels may be used, for example by grouping together the 25 pixels previously envisioned. In this case, a sensitivity of approximately three—five times higher—is obtained. This arises from the fact that the read noise of the camera is almost 25 times higher if 25 pixels are read individually than when they are grouped together into a single pixel.

Figure 10:
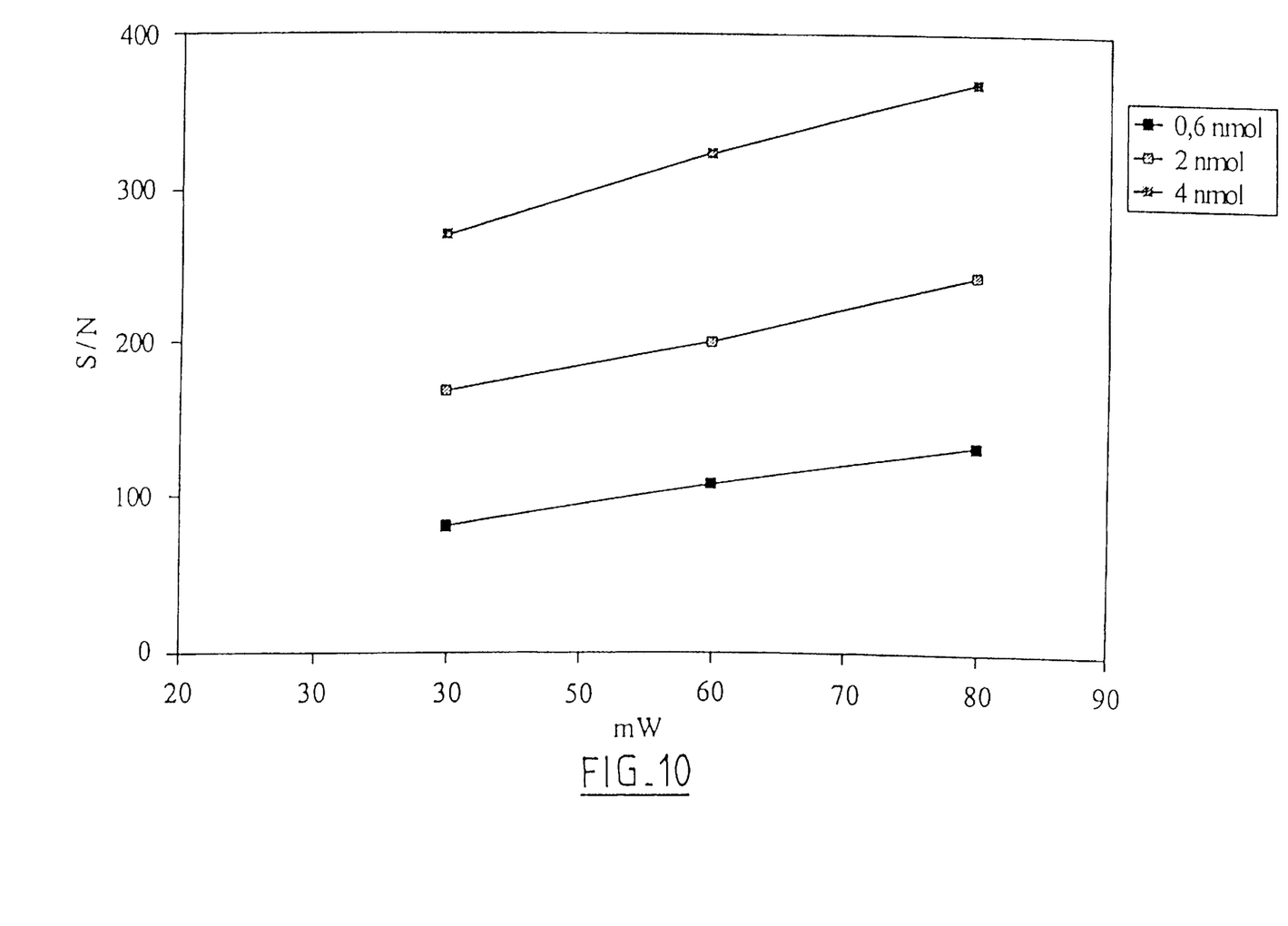
FIG. 10 is a graph on which the signal/noise ratio has been plotted as a function of the power of the laser, for three different fluorescein concentrations.

As may be observed in FIG. 10, it is also possible to gain in sensitivity by simply increasing the power of the laser. This shows that the system is not at its limit.

Figure 11:
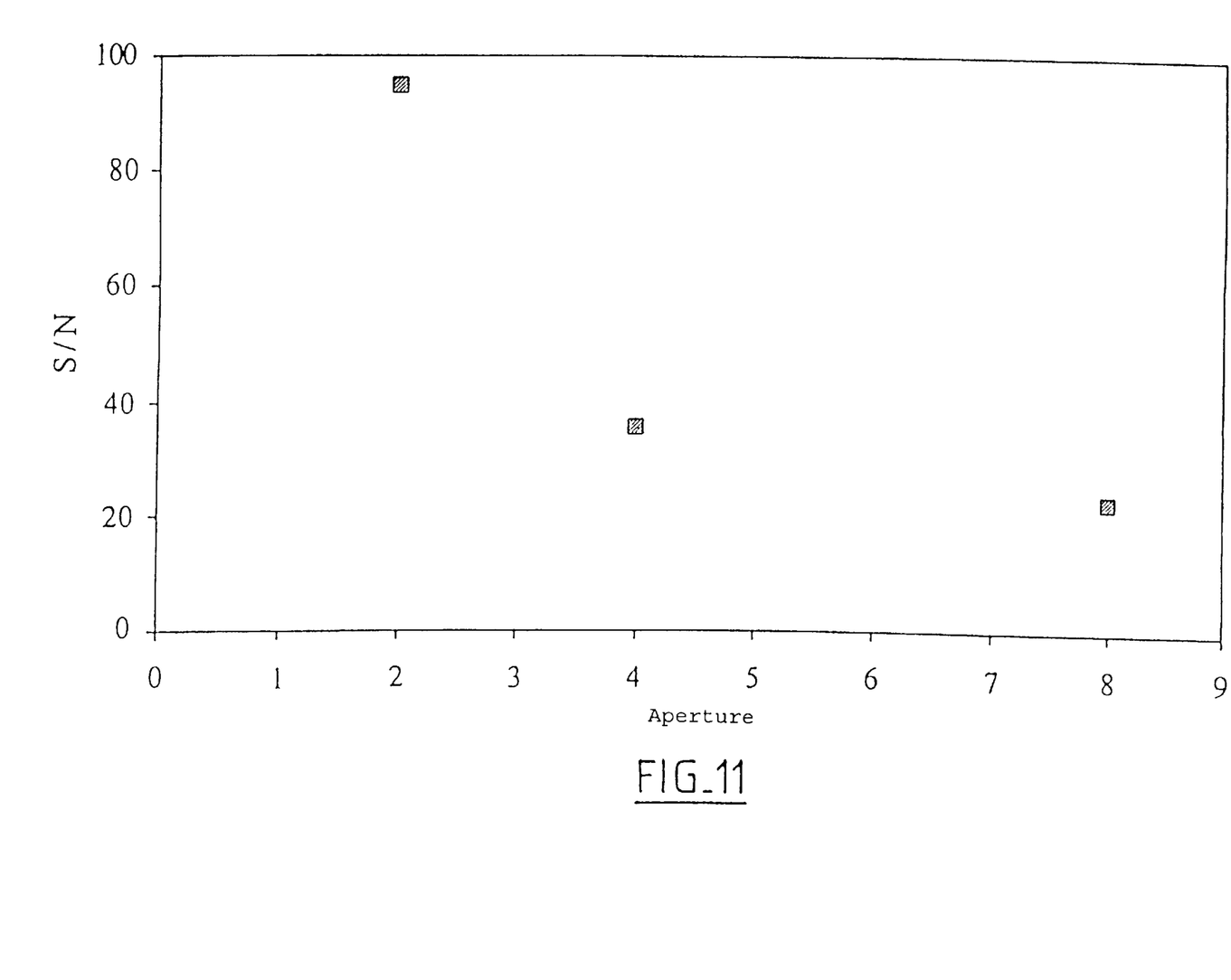
FIG. 11 is a graph on which the intensity of the signal/noise ratio has been plotted as a function of the aperture of the objective.

The dependence of the gathered light on the aperture of the objective was also tested. The signal/noise ratio is given for three different apertures of the objective in FIG. 11.

Moreover, the tests carried out by the inventors have shown that the sensitivity of the system also depended on the position of the point of impact of the laser with respect to the exit of the capillaries C. However, the latter varies little when the distance between said point of impact and the exit is varied from 2 mm to 250 $\mu$m, thereby confirming that essentially all the light exiting the opening of the capillaries C is effectively collected. In order to increase the sensitivity further, it would therefore be necessary for the beam F to be considerably closer to the exit of the capillaries C. Such a gain would entail poorer collimation of the light, which would in turn partially degrade the resolution of the image.

Figure 12A:
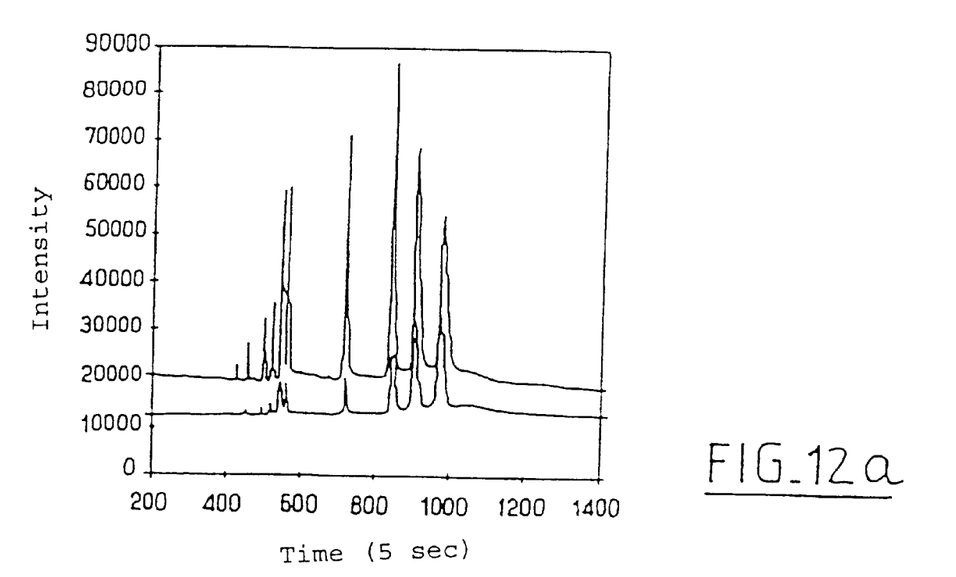
FIG. 12a is a graph on which the collected intensity has been plotted as a function of time for a specimen separation example used with the system illustrated in FIG. 1.

In order to demonstrate the capability of the system to separate the bands, the inventors carried out a migration test on the double-strand specimen ($\phi$X174 from Gibco BRL) in a polymer solution (0.5% HPC). The marker used was the SYBR(I) insert (from Molecular Probes). The result is plotted on the graph in FIG. 12a for two capillaries C. For a concentration of 1 ng/$\mu$l, the inventors obtained good separation of the bands and a good signal-to-noise ratio.

Figure 12B:
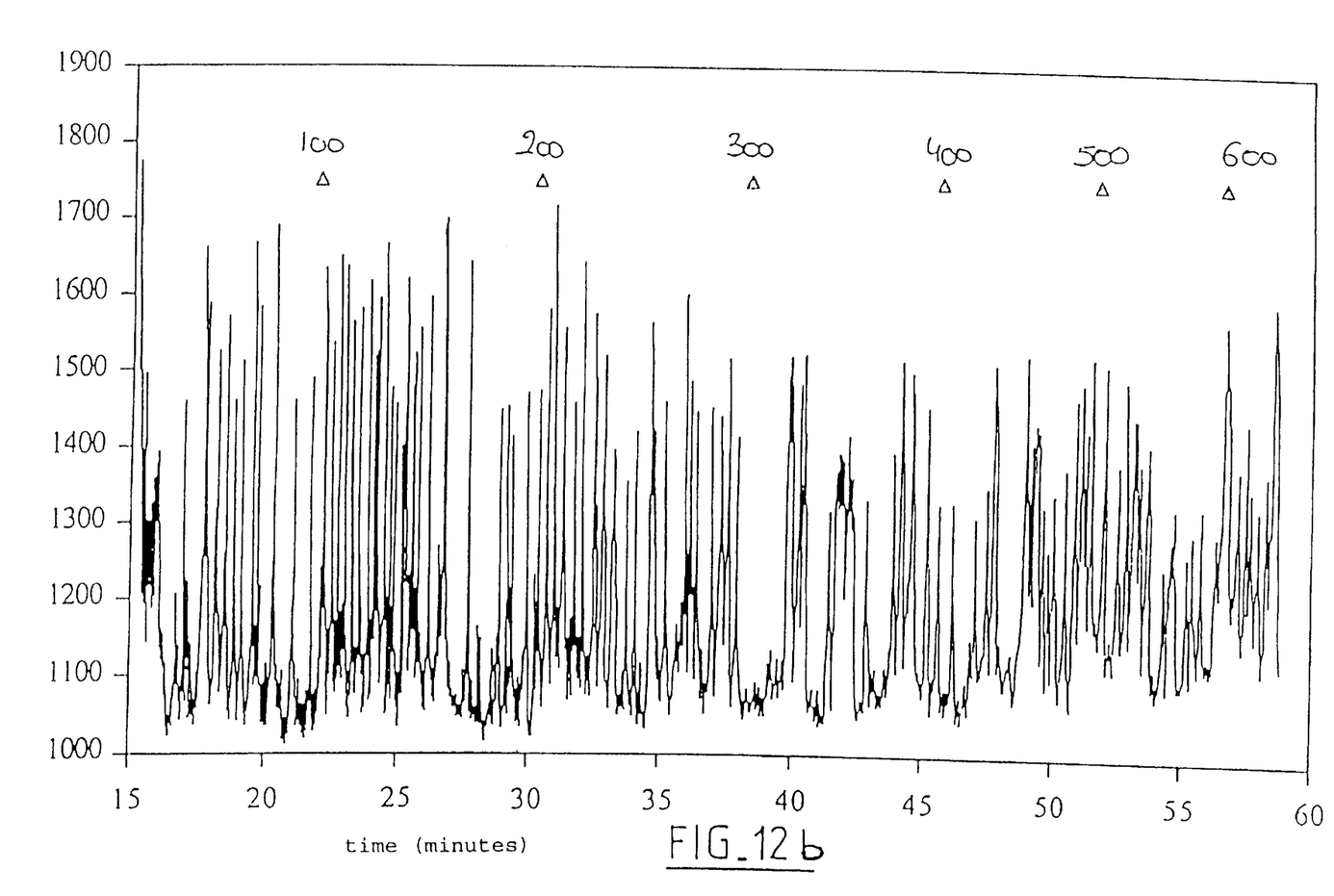
FIG. 12b is a graph on which the collected intensity has been plotted as a function of time for a DNA separation example used with the system illustrated in FIG. 1.

The inventors also carried out separation tests on a DNA specimen (M13) of a sequence reaction (T-terminator kit from AMERSHAM, primer labeled with FITC from PHARMACIA) in a polymer solution (5% T15 from the CURIE INSTITUTE) at 55° C. (FIG. 12b). The figure illustrates the quality of separation, the good signal-to-noise ratio and the separation rate (600 bases in 1 h).

Of course, variants other than the one just described may be envisioned. In particular, the fluorescence light beams exiting the capillaries C—which are collimated—may be directly transmitted to one or more intermediate prisms or else to a diffraction grating in order to spatially separate the various wavelengths emitted and to separate them on an array of photodiodes.

As will have been understood, the systems that have just been described are simple in design and allow high throughput to be achieved with great reliability and great ease of implementation.

What is claimed is:

1. A detection system for a multicapillary electrophoresis system comprising;

a plurality of juxtaposed capillaries, at least one source for the emission of a beam intended to excite molecules lying in its path and inside the capillaries and means for detecting the fluorescence of the molecules excited by said beam, wherein said means are arranged so as to detect the light which emerges at the exit of said capillaries and which propagates along the direction in which said capillaries extend and in that the resolution of the detection means is high enough to distinguish the light which emerges at the exit of the capillaries from that coming from the walls of the capillaries and/or from the medium which surrounds the capillaries.

2. The system according to claim 1, further including a matrix of capillaries, which includes said plurality of juxtaposed capillaries in at least one linear array.

3. The system according to claim 2, wherein the excitation beam is of elongate cross section and strikes several juxtaposed capillaries simultaneously.

4. The system according to claim 3, further including means for producing multiple focusing on a linear array of capillaries.

5. The system according to claim 4, wherein the beam exiting the side of one capillary is focused onto the adjacent juxtaposed capillary within the capillary array.

6. The system according to claim 5, wherein the space between the capillaries is filled, at least along the path of the excitation beam, with a material whose refractive index is chosen so that the excitation beam does not diverge after having traveled through a capillary.

7. The system according to claim 6, wherein said material is transparent and non-fluorescent.

8. The system according to claim 7, further including means for applying pressure in a detection cuvette, which pressure allows the capillaries to be filled with a separating matrix.

9. The system according to claim 8, further including dispersion means for spatially separating the various fluorescence wavelengths.

10. The system according to claim 9, wherein the detection means provide a complete image of the light exiting the capillaries.

11. The system according to claim 10, wherein the detection means further includes detection means of the charge-coupled device (CCD) type, as well as focusing means.

12. The system according to claim 10, wherein the detection means further includes detection means of the charge-coupled device (CCD) type, as well as a fiber bundle interposed between the exits of the capillaries and the detection means of the charge-coupled device type.

13. The system according to claim 4, wherein said means for producing multiple focusing on a linear array of capillaries is at least one microlens.

* * * * *